United States Patent [19]

Fleming

[11] Patent Number: 5,231,034
[45] Date of Patent: Jul. 27, 1993

[54] CUPRIC CHLORIDE ASSAY FOR DETECTION OF ANALYTES

[75] Inventor: Nigel Fleming, Boston, Mass.

[73] Assignee: McLean Hospital, Belmont, Mass.

[21] Appl. No.: 511,964

[22] Filed: Apr. 17, 1990

Related U.S. Application Data

[63] Continuation of Ser. No. 43,785, Apr. 29, 1987, abandoned.

[51] Int. Cl.$^5$ .......................................... G01N 21/29
[52] U.S. Cl. .................................... 436/169; 436/41; 436/80; 436/164
[58] Field of Search .................... 436/41, 80, 164, 169

[56] References Cited

U.S. PATENT DOCUMENTS

| | | | |
|---|---|---|---|
| 2,460,072 | 1/1949 | Davis | 436/41 |
| 4,221,785 | 9/1980 | Sorenson | 260/397.4 |
| 4,298,345 | 1/1981 | Sodickson et al. | 422/56 |
| 4,440,754 | 4/1984 | Sorenson | 424/140 |

FOREIGN PATENT DOCUMENTS 0070889  6/1977  Japan .................................. 436/80

OTHER PUBLICATIONS

Walmsley et al., "Between Alchemy and Technology," Prentice-Hall, Inc., Englewood Cliffs, N.J., pp. 71-75, 1975.
J. W. Mellor, "A Comprehensive Treatise on Inorganic and Theoretical Chemistry," vol. III, pp. 177-182, Longmans, Green and Co., 1940.
G. G. Hawley, "The Condensed Chemical Dictionary" 8th Ed., pp. 233-237, Van Nostrand Reinhold Company, 1976.
Fleming, N. et al., Anal. Biochem. 154: 691-701 (1986).
Feigl, F. (1949), Chemistry of Specific, Selective and Sensitive Reactions, Academic Press, N.Y., pp. 266-270, 345-350 and 369-377.
Wilson, E. W. et al., Arch. Biochem. Biophys. 142:445-454 (1971).
Blumberg, W. E. et al., J. Biol. Chem. 238:1675-1682 (1963).
Bryce, G. F. et al., J. Biol. Chem. 241:1439-1448 (1966).
Stricks, W. et al., J. Amer. Chem. Soc. 73: 1723-1727 (1951).
Drabikowski, W. et al., Arch. Biochem. Biophys. 181:359-361 (1977).
Lehrer, S. S. et al. Arch. Biochem. Biophys. 150:164-174 (1972).

Primary Examiner—Robert J. Warden
Assistant Examiner—Timothy M. McMahon
Attorney, Agent, or Firm—Sterne, Kessler, Goldstein & Fox

[57] ABSTRACT

The invention relates to a spot test method using a cupric chloride solution for detecting analytes in a sample which gives an immediate and distinctly colored reaction characteristic of the analyte. The invention also relates to a kit comprising the cupric chloride reagent.

10 Claims, 3 Drawing Sheets

CUPRIC CHLORIDE ASSAY FOR DETECTION OF ANALYTES This application is a continuation of application Ser. No. 07/043,785, filed Apr. 29, 1987, now abandoned.

FIELD OF THE INVENTION

The invention relates to an assay for analytes in solution. In particular, it is related to the detection of analytes by the formation of a colored reaction with cupric chloride.

BACKGROUND OF THE INVENTION

Many organic reagents form color precipitates with metal ions. The first report, in 1884, concerned the use of 1-nitroso-2-naphthol, as a precipitant for cobalt and other ions. Since then, colored ion reactions have played a key role in inorganic chemical analysis. A particularly intense color is associated with the formation of inner complex compounds, which are salts of metal atoms which manifest auxiliary valences towards certain atoms of a chelating acid radical. Nitrosophenylhydroxylamine, also known as cupferron, was one of the first organic reagents to be used for quantitative analysis which relied on the formation of inner complex salts. As illustrated by copper glycinate, copper salts can also form inner complex compounds. Many distinctive properties of metals not observed in normal salts appear upon formation of inner complex salts. Normally unstable compounds can be stabilized through inner complex formation. Inner complex compounds are especially important as analytical reagents, due to the formation of principal and auxiliary valence rings which frequently accompany anomalous solubility and/or tinctorial qualities. Feigl, F., *Chemistry of Specific, Selective and Sensitive Reactions*, Academic Press, N.Y. (1949).

Catalytic activity is exhibited by metals that can easily and reversibly change from one to another of several valences. Complex compounds often contain metals with valences which either do not occur in normal salts or which allow stable compounds to be formed with some unusual reagents. The remarkable discovery that copper (II) salts can catalyze reductions as well as oxidations is explained by alterations of valence to the unstable and strongly reducing Cu(I) ion, and to the unstable and strongly oxidizing Cu(III) ion. Feigl, supra.

A large variety of means for detecting copper, often at extreme dilutions, are based on the wide range of reactivity of copper ions. Hodgman, C. D. et al., *Handbook of Chemistry and Physics*, Chemical Rubber Publishing Co., Cleveland, Oh. (1962). Cavallini, D. et al., *Arch. Biochem. Biophys.* 124:18-26 (1968). Reagents employed in these assays include benzidine blue, salicylaldehyde and its oxime, mixtures of benzidine acetate and potassium bromide, cyanide, 8-hydroxyquinoline, phenylglycine, alpha amino-n-caproic acid and other amino acids, anthranilic acid, dicyandiamidine, 4-hydroxybenzothiazole, acyloinoximes, quinoline-8-carboxylic acid, precipitates such as rubeanates, iodine, and finally alpha-alpha'-alpha-tripyridyl. Partrington, J. R., *Textbook of Inorganic Chemistry*, 5th Ed., MacMillan and Co., London (1946). Feigl, F., supra.

Despite the extraordinary reactivity of copper ions with a wide variety of reagents, the use of copper as a reagent to test for other substances has been relatively limited. Cupric and cuprous salts have been utilized to detect mercaptobenzothiozole, sulfite, thiocyanate, xanthate, and thionalid. They have also been used as a reagent in gas analysis for carbon monoxide, ammonia, cyanide, and acetylene. Feigl, F., supra: Hodgman, supra: and Partrington, supra. The most conspicuous use of copper salts as analytical agents has been for the analysis of glucose and other sugars. At least eight chemical tests for sugars, some of them in tartrated media, have been published. Hodgman, C. D. et al., supra. These tests include Fehling's, Bang's, Barfoed's, Benedict's, Bertrand's, Hagedorm and Jensen's, Somogyi's, Nylander's, and Munsen and Walker's tests. Most of these tests utilize $CuSO_4$ as the primary reagent. However, these tests are especially laborious and require one or more heat steps followed by titration with a final reagent. Hodgman, C. D., supra.

Tartrated copper salts have also been utilized for years in the Lowry protein assay. Hodgman, C.D., supra. Despite the knowledge that a number of substances tend to cross-react in these assays, no effort has been made to exploit these other potentially specific reactions.

Traditional assays often require separate tests for individual analytes, which further require a number of steps and require spectrophotometric or other, sophisticated detection methods. For example, DTT is assayed by reaction with Ellman's reagent. Ellman, G. L., *Arch. Biochem. Biophys.* 82:70-77 (1959). McCloud, R. W., *Anal. Biochem.* 112:278-281 (1981). Cysteine may be assayed by spectrophotometric titration with ferricyanide which oxidizes cysteine to cystine, or by PCMB, o-iodosobenzoate, silver ion methods, or by monitoring $O_2$ consumption or $H_2O_2$ generation by cysteine-metal ion complexes. Cavallini, supra; Michaelis, L. et al., *J Biol. Chem.* 83:191-210 (1929). In addition, cystine and cysteine have been assayed using a uric acid reagent and sodium sulfite. Folin, O. et al., *J. Biol. Chem.* 83:103-108 (1929). Glycerol is usually determined by a two-step enzymatic assay. Bergmeyer, H.-U., *Methods of Enzymatic Analysis*, Academic Press, New York, N.Y. (1963). It would be desirable to have a test that allows for the simultaneous detection of all these analytes by a simple color test.

SUMMARY OF THE INVENTION

This invention relates to a method for detecting the presence of analytes in solution by the addition of aqueous cupric chloride to the solution and observing any colored reaction by visual or spectrophotometric means. The invention as well relates to a spot test which comprises application of a solution suspected of containing the analytes to filter paper impregnated with cupric chloride to give a colored reaction which may be analyzed by visual means.

The invention also relates to spot tests for analytes which require the further addition of aqueous NaOH, acetic acid or ammonium hydroxide to give the characteristic colored product. The invention also relates to a kit for the detection of analytes in solution.

This invention takes advantage of the ability of the cupric ion to form a large number of related colored compounds when mixed with a wide range of analytes. The invention offers a convenient, flexible, and rapid method to measure substances which are otherwise difficult to detect and quantify. In addition, the invention allows the use of simple and nontoxic reagents to simultaneously detect a number of analytes. Further, this invention can be used to quantitate the analytes that are being detected.

DESCRIPTION OF THE PREFERRED EMBODIMENTS

Figure 1:
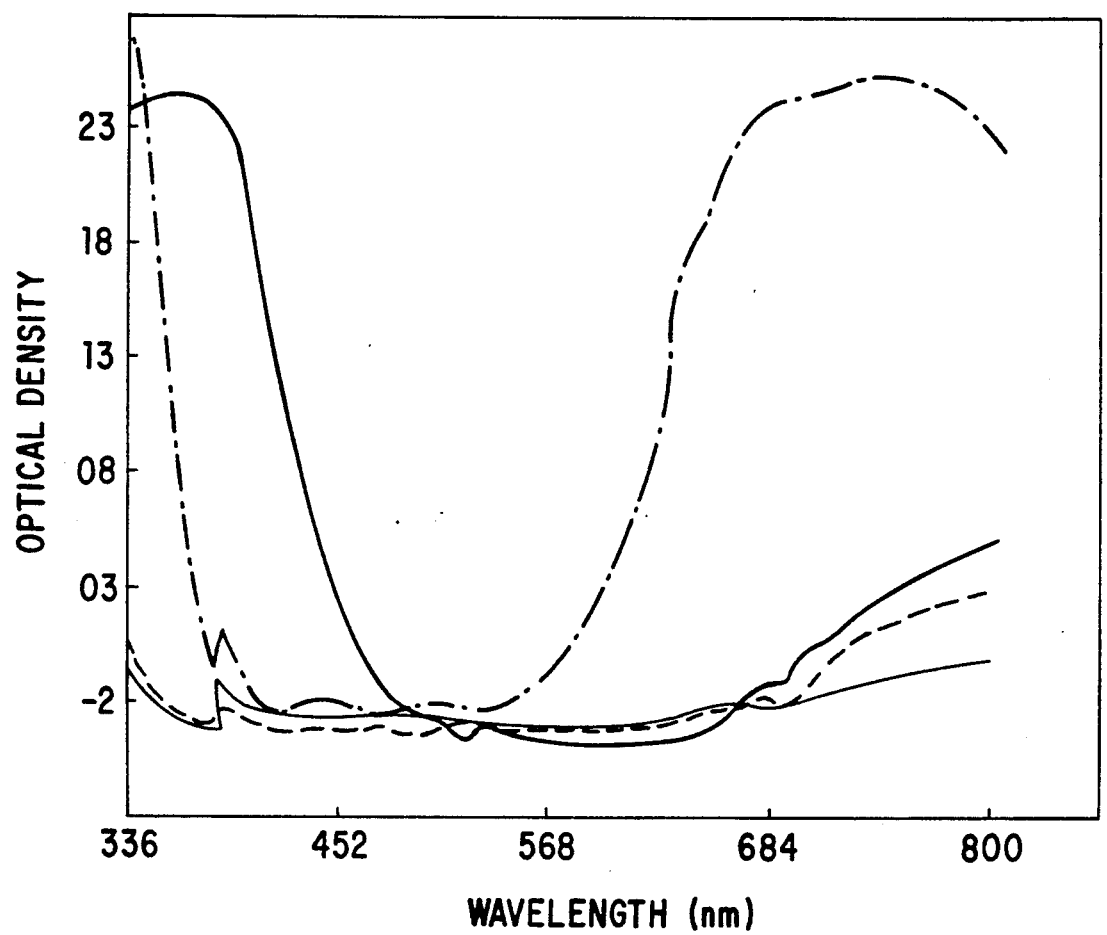
FIG. 1. This figure shows the wavelength maxima of the colored reaction obtained from EDTA, EGTA, sodium azide, and DTT dissolved in 50 mM Tris buffer, pH 7.4, in addition to a Tris buffer blank.

This invention is directed toward methods of assay using cupric chloride for determining the presence of an analyte in solution, which gives an immediate and distinctly colored reaction characteristic of the analyte. The methods of assay include both a solution test and spot test.

By the term "solution test" is intended a direct assay of a analyte by the simple contacting of the cupric chloride solution with the solution suspected of containing the analyte, which may optionally require the addition of a second working reagent, to yield an immediate color reaction indicating the presence of the analyte. By the term "spot test" is intended a direct assay of the assay by contacting a solution suspected of containing the analyte with a permeable solid support impregnated with cupric chloride, followed, optionally, by the addition of the second working reagent, to give an immediate color reaction characteristic of the analyte.

By the term "analyte" is meant a compound which gives a characteristic colored reaction or product when contacted with cupric chloride.

By the term "colored reaction" is intended a colored analyte-cupric complex which may comprise an insoluble precipitate or soluble product.

The method of this invention comprises contacting cupric chloride with a sample solution. The cupric chloride used in this invention is a solution of hydrated cupric chloride ($CuCl_2 \cdot 2H_2O$), dissolved in water, preferably distilled water. The concentration of cupric chloride in solution may be any that gives a colored reaction when contacted with the sample solution. This concentration of cupric chloride can be easily ascertained by routine screening, without undue experimentation. Preferably, the concentration of cupric chloride is from about 2% (w/v) to about 80% (w/v), more preferably from about 2% (w/v) to about 10% (w/v) for the solution test, and preferably about 20% (w/v) to about 80% for the spot test.

All related complexes of cupric chloride are colored. They may range from deep blue, to black, bright green, gray, yellow, turquoise, and red. Almost all these colors appear as products in the spot tests of this invention. Because of the unusual variety of colored properties which form with both organic and inorganic analytes, the cupric chloride is highly versatile in detecting a wide variety of analytes. Some products may further be distinguished by variations in solubility of the analyte-cupric complex.

Some analytes may further require the addition of a second reagent in order to generate a distinctly colored reaction. This second reagent may be any that will cause the formation of a colored reaction with the analyte-cupric complex or changes in the solubility thereof. For example, aqueous sodium hydroxide, ammonium hydroxide, and acetic acid may be used. In this aspect of the invention, the second reagent contacts the solution containing the analyte and cupric chloride to form a colored reaction or changes in solubility that may be visibly or spectrophotometrically detected. The second reagent that may be used in this invention, as well as the optimal concentration of the reagent to achieve maximal sensitivity, may be determined by routine screening, without undue experimentation. For example, the preferred concentration of aqueous sodium hydroxide is from about 0.5 N to about 2.0 N; aqueous ammonium hydroxide is from about 20% (v/v) to about 60% (v/v); and aqueous acetic acid is from about 20% (v/v) to about 60% (v/v).

Distinctive color reactions using cupric chloride were observed to occur with the following analytes ammonium bicarbonate, ammonium acetate, ammonium hydroxide, ammonium sulfate, ammonium persulfate, L-(+)-cysteine, dithiothreitol (DTT), ethylenediamine-N,N,N',N'-tetraacetic acid (EDTA), ethylene glycol bis(beta-aminoethyl ether)-N,N'-tetraacetic acid (EGTA), D-glucose, glycerol, imidazole, DL-methionine, mercaptoethanol, sodium azide, sodium dithionite, sodium metabisulfite, sodium nitrite, sodium periadate, sodium sulfite, sodium thiosulfite, sucrose, and N,N,N',N'-tetramethylethenediamine (TEMED). Most of these analytes are commonly used in the field of biochemistry. However, the invention is not limited to assay of just these analytes, it being within the contemplation of the invention to assay for any and all analytes which give a characteristic colored reaction or product when reacted with cupric chloride. Other analytes known to react with cupric ions, which may be analyzed by the methods of this invention include iridium and bisthmus salts, pyrrole-alpha-aldoxime, alpha-acyloinoximes, 1-nitroso-2-napthol, thioesters and thioketones, aliphatic azo compounds, sulfur dioxide, neocupoine, salicylaldehyde and its oxime, cyanide, 8-hydroxyquinoline, phenylglycine, alpha-amino-n-caproic acid and other amino acids, anthranilic acid, dicyandiamine, 4-hydroxybenzothiazole, acyloinoximes, quinoline-8-carboxylic acid, rubeanates, iodine and alpha-alpha'-alpha-tripyridyl. This assay may also be used for the detection and quantitation of thiols which include, but are not limited to penicilamine, L-cysteinediamine and L-cystinylbisglycine. This assay may also be used to detect the presence of common organic solvents.

In addition, the assay may be used to detect and quantify proteins. Such proteins include, but are not limited to, bovine serum albumin, D-glyceraldehyde-3-phosphate dehydrogenase, phosphoglucomutase, hemocyanin, ceruloplasmin, uricase and actin.

In one embodiment of this invention, a volume of a sample solution containing an analyte is contacted and mixed with an equal volume of a solution containing cupric chloride to give an immediate color reaction. After the reaction with cupric chloride, some compounds require the further addition of the second reagent in order to form a distinctly colored product. Thus, for example, glycerol, sodium metabisulfite, sodium thiosulfite, sucrose and glucose require the subsequent addition of the second reagent, sodium hydroxide.

Alternatively, the presence of the analytes may be detected by a spot test which comprises the application of small quantities of a sample solution to a permeable solid support which has been impregnated with cupric chloride. Such solid supports include, but are not limited to, filter paper. Individual drops of a cupric chloride solution are separately applied to the permeable solid support to form a reagent ring. The test sample is then added to the center of the ring while the cupric chloride solution is still damp or after it has been stored dry. If required, the second reagent is next added to the center of the ring and the mixture allowed to dry completely. Identification of the analyte may then be accomplished by comparison with similarly prepared standards and controls.

The invention also relates to the detection and quantitation of a plurality of analytes in a sample. This is accomplished by mixing the sample solution containing a plurality of analytes with an equal volume of a cupric chloride solution. Standard test samples can then be prepared, for example using either Tris buffer or water. In one embodiment of this invention, after contacting the sample solution with the cupric chloride solution, the mixture can be centrifuged. The pellet, after centrifugation, is then contacted with the second reagent. The colors should be noted of the mixture (sample and cupric chloride), pellet and supernatant, and pellet after second reagent. By comparison of the colors and solubilities obtained for each step, it is possible to determine the composition of a multi-component analyte mixture.

Alternatively, the test solution may be mixed with an equal volume of the cupric chloride, then with the second reagent. The color and the solubility of the colored reaction is noted, then the mixture is centrifuged. The colors of the pellet and the supernant are then noted. Again, by comparison of the colors and the solubility of the colored reaction obtained in each step above, it is possible to determine the composition of a multi-component analyte mixture. For example, using the above-described procedure, DTT, sodium azide, EDTA, and glucose were individually detected in a sample solution. However, the invention is not limited to assays for only these analytes, it being possible for one of ordinary skill in the art to prepare standards for other combinations of analytes for detection and quantitation, with no more than routine experimentation.

The spot test and solution test of the present invention finds utility as tests for analytes in a water source or supply. For example, the assay may be used to determine whether pollutants are present in drinking water. The tests also find utility as a means for detecting reagents commonly used in biochemistry. For example, the assay of the present invention may be utilized to determine whether the dialysate from a protein is free of analytes Thus, these assays provide a quick and easy method to determine whether the dialysis of a protein is complete.

The assay of the present invention is ideally suited for the preparation of a kit. Such a kit may comprise a carrier means being compartmentalized to receive in close confinement therein one or more container means, such as vials, tubes, and the like, each of said container means comprising one of the separate elements of the assay to be used in the method. For example, there may be provided a container means containing filter paper impregnated with cupric chloride or containing standard solutions of cupric chloride and container means containing standard solutions of the second reagent in addition to further carrier means containing standard solutions of varying concentrations of analytes to be detected. Standard solutions of cupric chloride preferably have concentrations from about 2–80% (w/v), more preferably from about 2–10%(w/v) for solution test and from about 20–80% (w/v) for the spot test.

The standard solutions of analytes may be used to prepare standard solution test of spot test colors for comparison with the sample, or may be used to prepare a standard curve with the concentration of the analyte plotted on the abscissa and the optical density of the colored reaction, obtained by spectrophotometry, on the ordinante. The results obtained from a sample containing one or more unknown analytes may be interpolated from such a plot to give the concentration of the analyte. To selectively quantitate more than one analyte, the optical density of the analytes may be determined at a number of wavelengths (FIG. 1). Where the reaction products have absorptions at different wavelengths, it is possible to separately detect and quantitate the analytes. Thus, for instance, it is possible to quantitate the EDTA reaction product at 684 nm without any significant interference from EGTA, DTT or sodium azide reaction products. At 500 nm, it is possible to quantitate sodium azide in the presence of DTT, EGTA and EDTA. The invention is not limited to selectively detecting the reaction product of EDTA or sodium azide, it being within the ability of one of ordinary skill in the art to determine other mixtures which allow the selective detection of a single analyte, with only routine experimentation.

The various aspects of the invention are further described by the following examples These examples are not intended to limit the invention in any manner.

EXAMPLES

EXAMPLE 1: ASSAY FOR ONE ANALYTE

Mercaptoethanol, Bis, TEMED, and acrylamide were purchased from Bio-Rad (N.Y.). Tris Trizma Base was purchased from Sigma Chemical Co. (St. Louis, Mo.). DTT was purchased from Boehringer (Indianapolis, Ind.). All other reagents were purchased either from Fisher (Medford, Mass.) or from Sigma Chemical Co. (St. Louis, Mo.). Ultrapure water was obtained from a Barnstead Nanopure water system (Millipore, Bedford, Mass.). Unless otherwise stated, reactions were performed in 12×75-mm polystyrene test tubes. Spectrophotometric analyses were made using quartz cuvettes in an LKB Ultraspec 4050 instrument equipped with Apple IIe software for spectral scans. Centrifugation was achieved using a benchtop clinical centrifuge at maximum speed for 4 minutes at room temperature.

The first working reagent, for use in a solution test, was prepared by dissolving 0.4 g of hydrated cupric chloride in 20 ml of distilled water. 400 ul of the test substance was mixed with an equal volume of the first working reagent to give an immediate color reaction, unless specified otherwise (Table 1). Standard test samples were prepared in either 50 mM tris buffer, pH 7.4, or in water as indicated (see Table Following centrifugation of the colored reaction product, the color of the pellet and of the supernatant (where present) were recorded. The pellet was then treated with the second working reagent (0.5 M NaOH) and the color noted.

Alternatively, the test solution (400 ul) was mixed with an equal volume of the first working reagent, then mixed with the second working reagent (500 ul). The color of the reaction product is noted, then the mixture is centrifuged. The colors of the pellet and the supernatant are noted. The combination of the supernatant and pellet colors allowed discrimination of analytes from other substances.

buffer was used instead of water. Sixteen of the substances tested formed a distinctive color reaction after addition of the first working reagent alone, whereas four required subsequent addition of aqueous sodium hydroxide. The compounds requiring this additional

TABLE 1
SOME REAGENTS GIVING DISTINCTIVE COLOR REACTIONS WITH COPPER CHLORIDE

| Mix | Substance | Limit of visual discrimination | Appearance after mix | Appearance after centrifugation | | Appearance after adding NaOH to supernatant | Appearance of NaOH-treated samples after centrifugation | |
|---|---|---|---|---|---|---|---|---|
| | | | | Pellet | Supernatant | | Pellet | Supernatant |
| 1. | H₂O blank | | Pale blue | (—) | Pale blue | Milky blue | Turquoise | Clear |
| 2. | Ammonium bicarbonate | 12.5 mM (0.1 w/v) | Milky pale blue | (—) | Blue | -C- | -C- | -C- |
| 3. | Ammonium acetate | 25 mM (0.19% w/v) | Clear blue | (—) | Clear blue | Light blue | Light blue | Violet |
| 4. | Ammonium hydroxide (30%) | (0.1% v/v) | Dark blue | Turquoise | Light violet | Dark blue | -C- | Light violet |
| 5. | Ammonium sulfate | (2%) | -C- | -C- | -C- | Dark blue | (—) | Dark blue |
| 6. | Ammonium persulfate | 0.022 mM (0.001% w/v) | -C- | -C- | -C- | Black | Black | Clear |
| 7. | L-(+)-Cysteine monohydrochloride | 0.07 mM (0.013% w/v) | Black flash ± dark gray | (—) or dark blue | Charcoal | Black | Dark blue | Charcoal |
| 8. | DTT | 1.25 mM (0.19% w/v) | Gray-green | Gray | Pale blue | Gray-green | Gray-green | Violet |
| 9 | EDTA | 0.6 mM (0.02% w/v) | Milky turquoise | Pale blue | Pale blue (A) | Milky dark blue | Blue | Pale violet |
| 10. | EGTA | 5.0 mM (0.19% w/v) | Milky turquoise | Turquoise | Blue | Milky light blue | Light blue | Clear |
| 11. | D-(+)-Glucose | 6 mM (0.1% w/v) | -C- | -C- | -C- | Clear dark blue | (—) | Clear dark blue |
| 12. | Glycerol (100%) | 0.3% (v/v)** | -C- | -C- | -C- | Muddy green to violet (D) | Orange at high concn. | Muddy green turning to orange |
| 13. | Imidazole | 12.5 mM (0.09% w/v) | Dark blue | Dark blue | Clear | Dark blue | Dark blue | Clear |
| 14. | Mercapto-ethanol (100%) | 0.049% (v/v) | Sulfur yellow ppt turning white | Yellow or white | Clear | Yellow/white ppt ppt in clear solution | Yellow/white | Clear |
| 15. | DL-Methionine | (100 mM) | Clear blue | (—) | Clear blue | Dark green | | Brown tint |
| 16. | Sodium azide | 19 mM (0.1% w/v) | Bright green ± brown ppt | Dark brown if present | Bright green | Green flash then milky blue | Gray-blue | Clear |
| 17. | Sodium dithionite | 0.25 (w/v) | Gray | Gray-green | Clear | Green | Green | Clear |
| 18. | Sodium metabisulfite | 25 mM** (1% w/v) | -C- | -C- | -C- | Bright green | Bright green | Clear |
| 19. | Sodium nitrite | 6.2 mM (0.04% w/v) | Bright green | (—) | Bright green | -C- | -C- | -C- |
| 20. | Sodium periodate | 3.1 mM (0.06% w/v) | Light green | Light green | Clear | Light green | Light green | Clear |
| 21. | Sodium sulfite | 12.5 mM (0.16% w/v) | Green | Dirty yellow | Clear | Dirty yellow | Dirty yellow | Clear |
| 22. | Sodium thiosulfate | 12.5 mM (0.6% w/v) | -C- | -C- | -C- | Bright green | Bright green | Clear |
| 23. | Sucrose | 6.0 mM** (0.4% w/v) | -C- | -C- | -C- | Clear blue | (—) | Blue |
| 24. | TEMED (100%) | (0.49% w/v) | Violet to blue | (—) at high concn., pale blue at low concn. | Violet | Clear violet | (—) | Violet |

Note: **Less blue than water blank treated identically; -C-, identical to water blank; (—), not present; (D), see Example 1 for further description. TEMED was tested in glass tubes because it reacts with plastic tubes. "Flash" refers to a colored product that may rapidly disappear when low concentrations of test compounds are analyzed.

Table 1 lists test substances that gave distinctive color reactions when cupric chloride solution was added followed by addition of the second working reagent before or after (added to pellet) centrifugation. The limit of visual discrimination refers to the concentration at which the test substance in water can still be discriminated from a water blank treated in an identical manner to the sample. Similar results were obtained when Tris buffer was used instead of water. Sixteen of the substances tested formed a distinctive color reaction after addition of the first working reagent alone, whereas four required subsequent addition of aqueous sodium hydroxide. The compounds requiring this additional step were glycerol, sodium metabisulfite, sodium thiosulfite, sucrose, and glucose. These reaction products persisted following subsequent addition of sodium hydroxide, except for sodium nitrite and ammonium bicarbonate, where the sodium hydroxide reaction products were identical to water controls. Some analytes produced unstable reaction products when present in low concentrations. For example, glycerol reacted with the first and second working reagent at dilutions less than 1:8 by initially turning violet, then becoming muddy green within approximately 1 minute, and then developed a rust-colored precipitate in a clear solution. Dilutions of glycerol between 1:32 and 1:64 produced little or no precipitate and gave a violet supernatant. At dilutions greater than 1:128, a bright blue precipitate formed which was distinguished from control samples by the presence of a violet supernatant. Mercaptoethanol produced a sulfur-yellow precipitate when combined with the first working reagent. This color then gradually changed to pale yellow or white. Ammonium persulfate developed a striking black precipitate. At lower concentrates of persulfate, longer periods of time were needed to develop the reaction product color. Some reaction products were very ephemeral when the test substance was at low concentrations. These are listed as "flash reactions." Cysteine reacted with cupric chloride instantaneously to develop a black product which persisted only for a few seconds. Sodium azide formed a transitory green product on addition of cupric chloride, before turning milky blue.

Most of the substances that did form distinctive color reactions could be selectively discriminated at a concentration of 0.2% or less. Some analytes afforded considerably more sensitive detection limits. In particular, TEMED and mercaptoethanol were detected at concentrations of 0.49%, imidazole at 0.09% (12.5 mM), sodium periodate at 0.06% (3.1 mM), sodium nitrite at 0.04% (6.2 mM), EDTA at 0.02% (0.6 mM), cysteine monohydrochloride at 0.013% (0.07 mM) and ammonium persulfate at 0.001% (0.022 mM).

A variety of substances formed colored products that could not be distinguished from water blanks when tested at concentrations up to 10 mg/ml. These substances included 50 mM Tris buffer, pH 7.4, ammonium bicarbonate, urea, Bis, isopropyl alcohol, 30% SDS, sodium fluoride, 5% TCA, phenol, dibasic potassium phosphate, methyl alpha-D-mannopyranoside, guanidine hydrochloride, chloramine T, magnesium chloride, boric acid, and 0.1 M hydrochloric acid.

Two reagents were observed to exhibit distinctive reactions without forming a colored product. The addition of hydrogen peroxide to the working reagent caused a strongly exothermic reaction for 1-2 minutes. Triton X-100 formed two phases with the first working reagent. A precipitate formed between the two layers by layering aqueous sodium hydroxide (the second working reagent) on the interface between the layers.

FIG. 1 depicts the absorption maximum of DTT, sodium azide, EDTA, EGTA, 50 mM Tris buffer, pH 7.4, and a water blank after the addition of the first working reagent followed by centrifugation. The lines on the graph represent the following: (---) EDTA and EGTA; (-) blank; (· · ·) DTT; (—) sodium azide.

EXAMPLE 2: QUANTITATION OF DDT AND SODIUM AZIDE BY SPECTROPHOTOMETRY.

Spectrophotometric assays for the quantitation of DTT and sodium azide were also developed. Serial dilutions of DTT were mixed with an equal amount of the first working reagent according to Example 1, centrifuged, and the optical density of the resulting supernatant determined. The results appear in Table 2 below.

TABLE 2

| DTT STANDARDS | |
|---|---|
| Concentration DTT (mM) | Optical Density (817 nm) |
| 5.0 | 4 |
| 2.5 | 0.56 |
| 1.0 | 0.66 |
| 0 | 0.70 |

Figure 2:
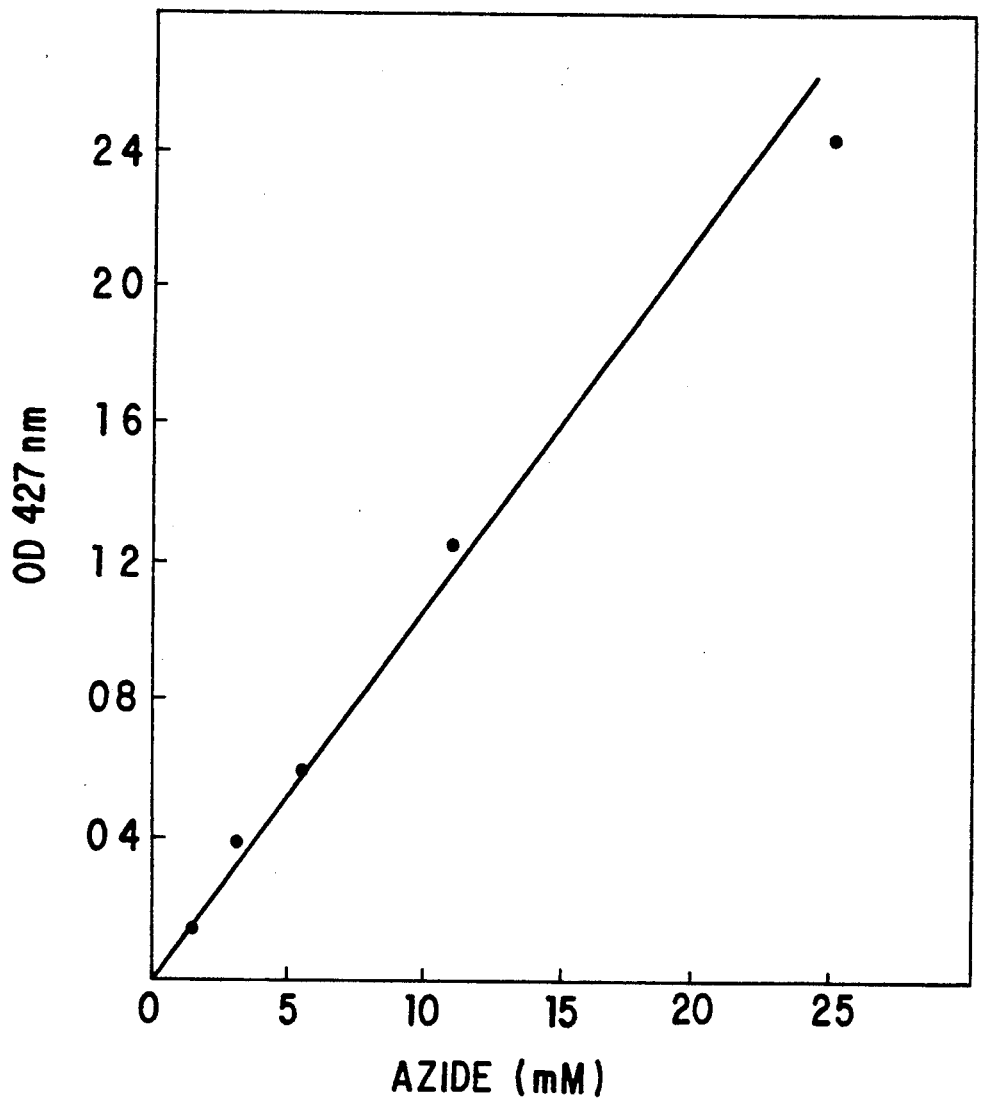
FIG. 2. This figure shows the standard curve for sodium azide obtained by plotting the optical density of the sodium azide colored reaction against the concentration of sodium azide.

The standard curve for sodium azide is depicted in FIG. 2. Solutions of 1, 3, 5, 10 and 25 mM sodium azide were treated according to Example 1, centrifuged, the supernatant (600 ul) combined with distilled water (400 ul) and analyzed spectrophotometrically at 427 nm in quartz cuvettes. The standard curve is linear from 11 to at least 40 mM sodium azide.

EXAMPLE 3: SPOT TEST FOR SMALL SAMPLES.

Figure 3:
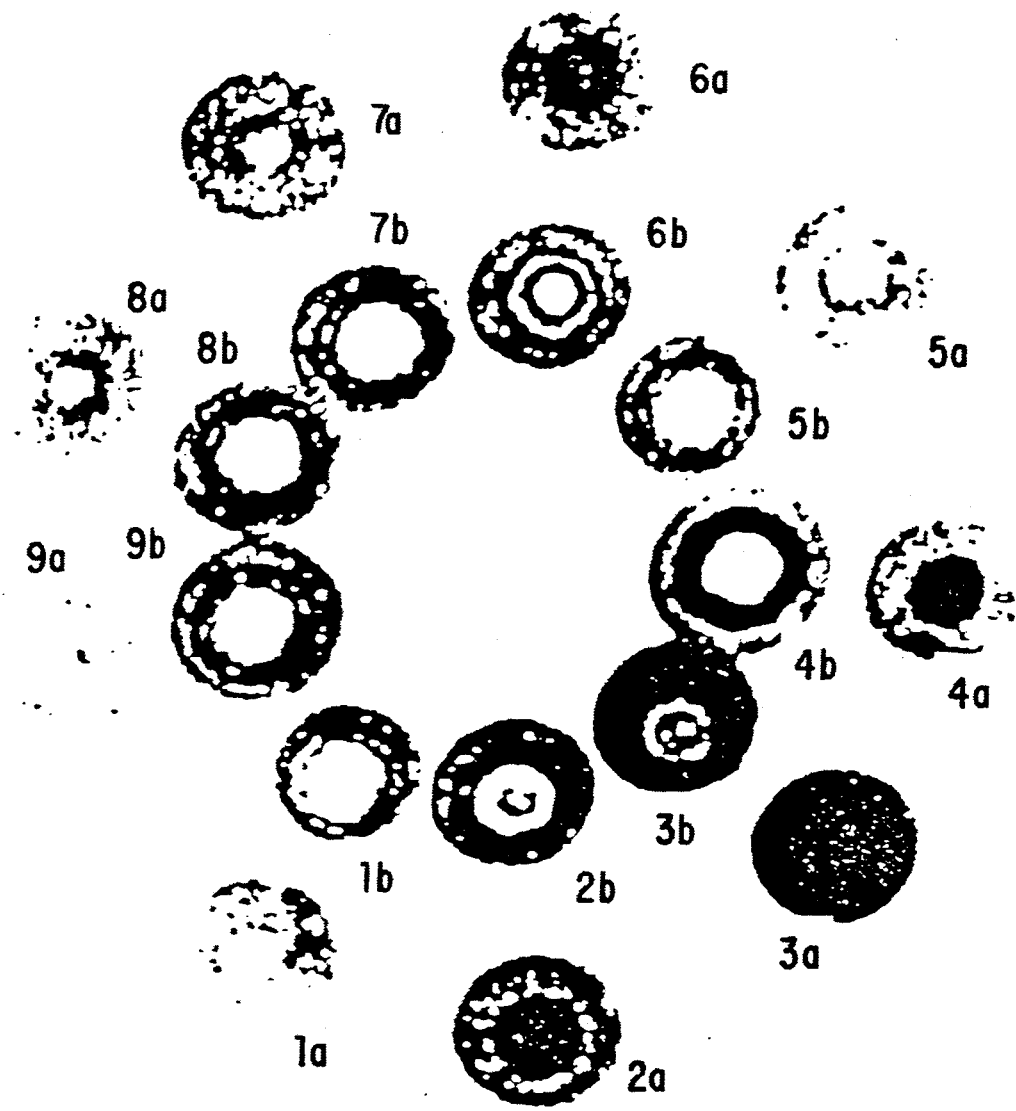
FIG. 3. This figure shows the results of a spot test using reagent-impregnated filter paper.

Spot tests were developed for small quantities (5 ul) of test sample by application to filter paper impregnated with cupric chloride as follows. Individual 20-ul drops of cupric chloride, at either 4.0 g/20 ml (light blue), or at 16 g/20 ml (green), were placed on Whatman 41 filter paper to form a 2-cm reagent ring. Five ul of test sample was then added to the center of the ring (series a) while the reagent was still damp, or after it had been stored dry in duplicate. In addition, 10 ul of 0.5 N NaOH was applied to a duplicate spot (series b) and the mixture allowed to dry completely. The results were then compared to similarly prepared standards. FIG. 3 depicts the results of a filter paper spot test for nine different compounds using the 0.4 g/5 ml reagent spot. The following analytes were tested: 1) water control; 2) DTT (100 mM); 3) TEMED (100%); 4) sodium thiosulfate (100 mM); 5) cysteine (10 mg/ml); 6) ammonium hydroxide (100%); 7) sucrose (100 mM); 8) EDTA (100 mM); 9) sodium periodate (100 mM). The concentration selected for adequate contrast in FIG. 3 is higher than required for visual discrimination in color. Since only 5 ul of a test sample is required to produce a 1 to 2-cm ring, this test resulted in increased sensitivity of the assay. Even in the black and white representation of FIG. 3, it may be appreciated that distinctive reaction products are readily apparent. As the 5-ul test sample was added to the filter paper impregnated with the test reagent, the reaction products were effectively chromatographed into a series of colored rings according to their mobility and solubility. These rings changed color during drying, presumably because of reaction with atmospheric oxygen. It was found that the combined use of cupric chloride spots at two concentrations was more effective for detection of analytes such as TEMED, ammonium hydroxide and ammonium thiosulfate which are more easily visualized at higher concentrations of cupric chloride. In contrast, compounds like DTT are somewhat more readily visualized using the lower concentration of working reagent.

EXAMPLE 4: ASSAY FOR COMBINATIONS OF ANALYTES WITH CUPRIC CHLORIDE.

Mixtures of one or more of four representative analytes (sodium azide, DTT, glucose and EDTA) were diluted in water and analyzed with cupric chloride according to Example 1. As shown in Table 3, it was possible to discriminate between various combinations of these analytes, by comparison of the colored reactions.

TABLE 3

ASSAY FOR COMBINATIONS OF ANALYTES WITH CUPRIC CHLORIDE

| Mix | Substance | Appearance after mix | Appearance after contrifugation | | Appearance after adding NaOH (mix pellet in) | Appearance of NaOH-treated samples after centrifugation | |
|---|---|---|---|---|---|---|---|
| | | | Pellet | Supernatant | | Pellet | Supernatant |
| 1. | H₂O control | Very very light blue | (—) | Very very light blue | Milky blue | Bright blue | Clear |
| 2. | DTT 25 mM | Gray-green ppt, pale s/n* | Pale green | Clear | Milky blue-green | Green-blue | Clear |
| 3. | Sodium azide 0.025% | Clear bright green | (—) | Clear bright green | -C- | -C- | -C- |
| 4. | EDTA 2.5 mM | Milky turquoise | Pale blue | Light blue | -C- | -C- | -C- |
| 5. | D-Glucose 25 mM | Milky turquoise | -C- | -C- | Clear dark blue | (—) | Clear dark blue |
| 6. | D-Glucose 25 mM Sodium azide 0.025% | Milky green | (—) | Milky green | Clear darkish blue | (—) | Clear darkish blue |
| 7. | D-Glucose 25 mM DTT 25 mM | Gray-green ppt, pale s/n* | Pale green | Clear | Blue-green | Small black pellet | Dark blue |
| 8. | D-Glucose 25 mM EDTA 2.5 mM | Milky turquoise | Pale blue | Light blue | Clear turquoise | Small white pellet | Clear turquoise |
| 9. | EDTA 2.5 mM Sodium azide 0.025% | Very milky green | Bright green | Clear green | Milky darker blue | Bright blue | Tint of blue |
| 10. | EDTA 2.5 mM DTT 25 mM | Gray-green ppt, greenish s/n* | Gray-green | Greenish | Milky dark green | Gray-green | Tint of purple |
| 11. | Sodium azide 0.025% DTT 25 mM | Dirty green ppt, green s/n* | Gray | Green | Milky dark green | Gray-green | Tint of purple |
| 12. | D-Glucose 25 mM EDTA 2.5 mM Sodium azide 0.025% | Very milky green | Bright green | Green | Clear Prussian blue | (—) | Clear Prussian blue |
| 13. | EDTA 2.5 mM Sodium azide 0.025% DTT 25 mM | Black ppt, green s/n* | Black | Green | Milky gray-green | Gray-green | Light purple |
| 14. | DTT 25 mM D-Glucose 25 mM EDTA 2.5 mM | Gray-green ppt, greenish s/n* | Gray-green | Greenish | Milky dark gray-blue | Black | Prussian blue |
| 15. | D-Glucose 25 mM DTT 25 mM Sodium azide 0.025% | Dirty green ppt, greenish s/n* | Gray | Bright green | Milky darker green-blue | Black | Prussian blue |
| 16. | D-Glucose 25 mM EDTA 2.5 mM Sodium azide 0.025% DTT 25 mM | Black ppt, green s/n* | Black | Bright green | Milky darker green | v. dark green | Prussian blue |

Note: The concentrations indicate the final concentration of analytes in the test sample (400 ul). The assay was performed as described in Example 3. The precipitate following centrifugation was resuspended before addition of the second working reagent (0.05 M NaOH). All dilutions were made in water, and the results compared to a water blank, listed at the top of the table.
*s/n, supernatant

EXAMPLE 5: USE OF CUPRIC CHLORIDE TEST TO DETERMINE EXTENT OF REAGENT CONTAMINATION DURING PURIFICATION OF A PROTEIN

This assay was used to discriminate the presence of sodium sulfate in a pigmented protein solution up to 4% in a 50 mM tris buffer solution containing 5 mM DTT and 5 mM EDTA during the early steps of purification of calcium-inactivated neutral protease. The assay was carried out according to Example 1. The high protein concentration (greater than 1 mg/ml), which formed an insoluble deposit at the center of the reagent circle when applied to cupric chloride impregnated filter paper, did not permit symmetrical addition of sodium hydroxide. Vitto, A. and Nixon, R. A., *J. Neurochem* 47:1039-1051 (1986).

Having now fully described this invention, it will appreciated by those skilled in the art that the same can be performed within a wide range of equivalent parameters of concentrations, conditions, and methods of characterizing the resulting reagent complexes, without departing from the spirit or the scope of the invention or any embodiment thereof.

What is claimed is:

1. A method for detecting more than one analyte in solution, comprising
   (a) contacting a sample solution suspected of containing more than one analyte with a sufficient concentration of cupric chloride in water to cause the formation of a colored reaction;
   (b) detecting said colored reaction in the mixture of said sample and cupric chloride;
   (c) centrifuging said mixture to obtain a pellet and a supernatant, and
   (d) detecting the colors of said pellet and said supernatant and thereby detecting said analytes.

2. A method for detecting more than one analyte in solution, comprising
   (a) contacting a sample solution suspected of containing more than one analyte with a sufficient concentration of cupric chloride in water to cause the formation of a colored reaction;
   (b) detecting said colored reaction in the mixture of said sample and cupric chloride;
   (c) contacting said mixture with a second reagent selected from the group consisting of aqueous sodium hydroxide, aqueous acetic acid, and ammonium hydroxide to give a colored reaction;
   (d) centrifuging said mixture and second reagent, and
   (e) detecting the colors of the resultant pellet and supernatant.

3. The method of claim 1, further comprising e) contacting said pellet obtained from step d) with a second reagent to cause the formation of a colored reaction;

f) detecting said colored reaction.

4. The method of claim 3 or 4, wherein said second working reagent is selected from the group consisting of aqueous sodium hydroxide, aqueous acetic acid and aqueous ammonium hydroxide.

5. The method as in any one of claims 1, 2, or 3 wherein said colored reaction is compared with colored reactions formed with standard solution of said analyte.

6. The method as in any of claims 1, 2, or 3 wherein said analyte is detected by visual comparison of said colors with those of said standards.

7. The method as in any one of claims 1, 2, or 3 wherein said analyte is detected by spectrophotometric detection.

8. The method as in any one of claims 1, 2, or 3 wherein said analyte is detected quantitatively.

9. A method for detecting and identifying more than one analyte in solution, comprising
  (a) contacting a sample solution suspected of containing more than one analyte with a solution comprising 2 to 80% (w/v) cupric chloride in water to give a colored reaction product;
  (b) centrifuging said colored reaction product obtained in step (a) to give a colored pellet and a colored supernatant;
  (c) separating said colored pellet from said colored supernatant;
  (d) contacting said colored pellet obtained from step (c) with a second working reagent to give a colored reaction product, wherein said second working reagent is selected from the group consisting of aqueous sodium hydroxide, aqueous acetic acid, and aqueous ammonium hydroxide; and
  (e) detecting and identifying said analytes by comparing the color of said reaction product of step (a), said colored pellet and said colored supernatant of step (b), and said colored reaction product of step (d), to the colors obtained from solutions of suspected analytes.

10. A method for detecting and identifying more than one analyte in solution, comprising
  (a) contacting a sample solution suspected of containing more than one analyte with a solution comprising 2 to 80% (w/v) cupric chloride in water to give a colored reaction product;
  (b) contacting said colored reaction product obtained in step (a) with a second working reagent to give a second colored reaction product, wherein said second working reagent is selected from the group consisting of aqueous sodium hydroxide, aqueous acetic acid, and aqueous ammonium hydroxide;
  (c) centrifuging said second colored reaction product obtained in step (b) to give a pellet and colored supernatant;
  (d) detecting and identifying said analytes by comparing th color of said reaction product of step (a), said second colored reaction product of step (b), and said colored pellet and colored supernatant obtained in step (c) to the colors obtained from standard solutions of suspected analytes.

* * * * *